US012673082B2

(12) United States Patent
Hwang et al.

(10) Patent No.: US 12,673,082 B2
(45) Date of Patent: Jul. 7, 2026

(54) **USE OF *Bletilla formosana* (HAYATA) SCHLTR. EXTRACT FOR THE MANUFACTURE OF A PHARMACEUTICAL COMPOSITION FOR PROMOTING CHRONIC WOUND HEALING**

(71) Applicant: Chang Gung University of Science and Technology, Taoyuan City (TW)

(72) Inventors: Tsong-Long Hwang, Taoyuan City (TW); Yu-Chia Chang, Taoyuan City (TW)

(73) Assignee: Chang Gung University of Science and Technology, Taoyuan City (TW)

( * ) Notice: Subject to any disclaimer, the term of this patent is extended or adjusted under 35 U.S.C. 154(b) by 380 days.

(21) Appl. No.: 18/482,014

(22) Filed: Oct. 5, 2023

(65) Prior Publication Data

US 2024/0123017 A1     Apr. 18, 2024

Related U.S. Application Data

(60) Provisional application No. 63/379,144, filed on Oct. 12, 2022.

(51) Int. Cl.
| | |
|---|---|
| *A61K 36/00* | (2006.01) |
| *A61K 36/898* | (2006.01) |
| *A61P 17/02* | (2006.01) |

(52) U.S. Cl.
CPC ............ *A61K 36/898* (2013.01); *A61P 17/02* (2018.01)

(58) Field of Classification Search
None
See application file for complete search history.

(56) References Cited

FOREIGN PATENT DOCUMENTS

| | | |
|---|---|---|
| CN | 1613489 A | 5/2005 |
| WO | PCT/CN2022/082715 | 3/2022 |

OTHER PUBLICATIONS

Raskin et al. (2004) Current Pharmaceutical Design 10: 3419-3429. (Year: 2004).*
Revilla et al. (1998) J. Agric. Food Chem. 46: 4592-4597. (Year: 1998).*
Deng et al. (2021) Oxidative Medicine and Cellular Longevity, vol. 2021 Article ID 8852759 (11 pages) (Year: 2021).*
Fan et al. (2023) Medicinal Plant Biology 2:21 (21 pages). (Year: 2023).*
Gu et al. (2022) Carbohydrate Polymers 292: 119694 (14 pages). (Year: 2022).*
Li et al. (2024) Food Bioscience 60 : 104339 (12 pages) (Year: 2024).*
Wu et al. (2010) J. Food and Drug Analysis vol. 18, No. 4: 279-289. (Year: 2010).*
Spampinato S. et al., The Treatment of Impaired Wound Healing in Diabetes: Looking among Old Drugs, Pharmaceuticals 2020, 13, 60.
Lai T. et al., Study of the Chinese herb *Bletilla striata* on wound healing, Taiwan Journal of Chinese Medicine, Sep. 2002.
Chen Y., Effect of Bletilla striata on cutaneous wound healing, Thesis of institute of China medical, China medical college, 2002.
Chen Y. et al., The Development, Cultivation and Chemical Constituents in Psudobulbs of *Bletilla formosana* (Hayata) Schltr. Research Report of Taichung District Agricultural Improvement Station, vol. 103 (Jun. 2009).
Cheng J. et al., Research and Application of the Mechanism of Traditional Chinese Medicine in Wound Healing, Research Report on Special Research Projects Subsidized by the Ministry of Science and Technology, MOST, End-of-term report, 106-2320-B-077-004, (Oct. 5, 2018).
Zhao Y. et al., Research Progress on the Wound-Healing Effects of Bletilla striata Journal of Chinese Medicinal Materials, vol. 43, (Apr. 2020).
Chen M., Study on Quality Evaluation of Bletilla Rhizoma Chengdu University of Traditional Chinese Medicine, Master's degree thesis, May 2017.
Lu M. et al., Application of polysaccharides isolated from non-medical parts of Bletilla formosana, International Conference on Biochemistry and Molecular Biology, ICBMB, Apr. 2019.
Cheng J. et al., Study for chemical composition and wound repair activity of Bletilla formosana polysaccharide, Proceedings for Annual Meeting of The Japanese Pharmacological Society, WCP2018:PO3-6-23, (Jul. 2018).
Lin C. et al., Chemical Constituents of the Rhizomes of Bletilla formosana and Their Potential Anti-inflammatory Activity, Journal of Natural Products, 2016, 79, 1911-1921.
Song Y. et al., In vivo wound healing and in vitro antioxidant activities of Bletilla striata phenolic extracts, Biomedicine & Pharmacotherapy 93 (2017) 451-461.
Yang C. et al., Using the UPLC-ESI-Q-TOF-MS method and intestinal bacteria for metabolite identification in the nonpolysaccharide fraction from Bletilla Striata, Biomedical Chromatography, 2019; 33:e4637.

* cited by examiner

*Primary Examiner* — Russell G Fiebig
(74) *Attorney, Agent, or Firm* — Hannah Tien

(57) ABSTRACT

A method for promoting chronic wound healing is provided, including administering an effective amount of *Bletilla formosana* (*Hayata*) Schltr. extract to a subject in need thereof, wherein the effective amount of *Bletilla formosana* (*Hayata*) Schltr. extract is 0.01 mg/kg-body weight to 100 mg/kg-body weight, and wherein the chronic wound including diabetic wound and Diabetic Foot Ulcer.

9 Claims, 6 Drawing Sheets
(2 of 6 Drawing Sheet(s) Filed in Color)

Figure 1A
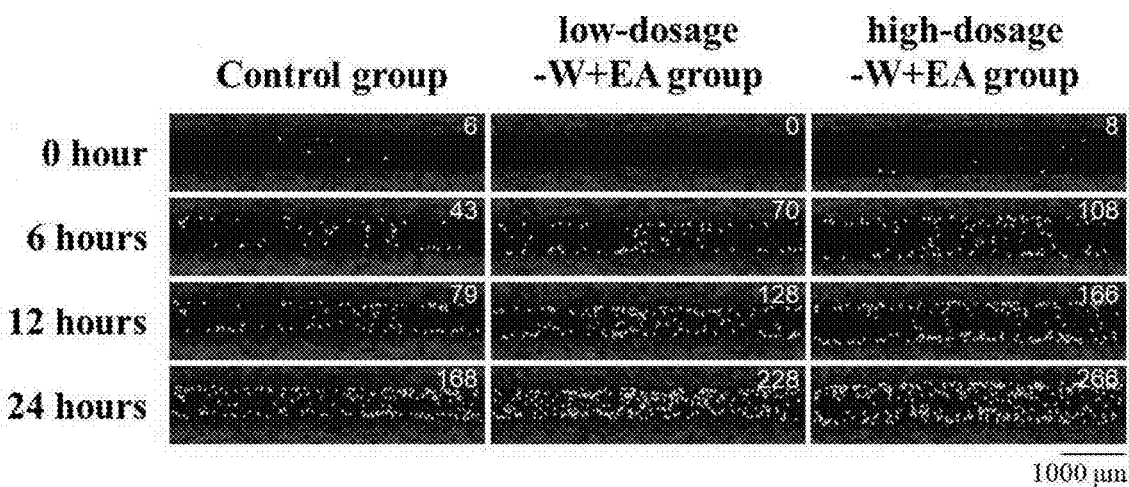
Figure 1B
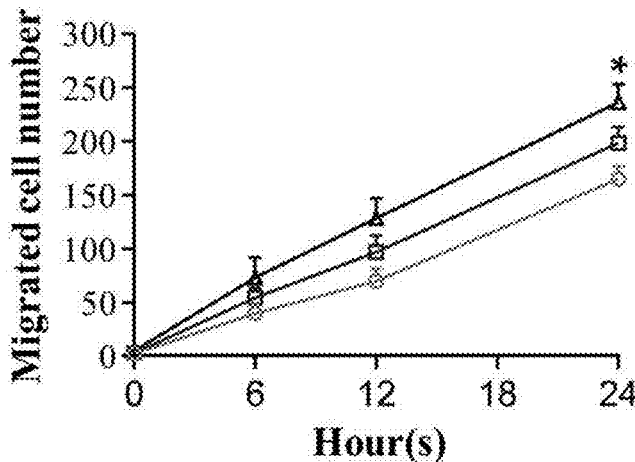
*Compared with Control group
Figure 1

USE OF Bletilla formosana (HAYATA) SCHLTR. EXTRACT FOR THE MANUFACTURE OF A PHARMACEUTICAL COMPOSITION FOR PROMOTING CHRONIC WOUND HEALING

CROSS-REFERENCE TO RELATED APPLICATION

This application claims the benefit of U.S. Provisional Patent Application No. 63/379,144 filed on Oct. 12, 2022, which is incorporated by reference herein in its entirety.

FIELD OF THE INVENTION

The present invention relates to a method for promoting chronic wound healing by administering an effective amount of plant extract to a subject in need thereof, particularly to a method for promoting chronic wound healing by administering an effective amount of Bletilla formosana (Hayata) Schltr. extract to a subject in need thereof.

BACKGROUND OF THE INVENTION

Diabetes mellitus (DM) is a metabolic disease which is caused by damage of insulin and/or the insulin generating function and therefore leads hyperglycemia. People with DM often have a number of complications, one of which is impaired self-healing.

The disorder of the wound healing of diabetes is related to various factors such as vascular degeneration, neuropathy, immune and biochemical ingredients. Hyperglycemia causes sclerosis of vessels, which leads to slower circulation and microvascular dysfunction, and causes reduction of tissue oxygenation. Hyperglycemia also reduces the migration of white blood cells to the wound, so DM patients are more vulnerable to infection, and the peripheral neuropathy in DM may cause numbness in the region and decrease in the ability to feel pain, which may cause the wound to not be immediately noticed and take appropriate treatment (Spampinato S F, Caruso G I, De Pasquale R, Sortino M A, Merlo S. The Treatment of Impaired Wound Healing in Diabetes: Looking among Old Drugs. Pharmaceuticals (Basel). 2020; 13(4):60).

It is noteworthy that Diabetic Foot Ulcer (DFU) is the main complication of DM and occur in 15% of diabetic patients. The risk factors related to DFU are considered neuropathy, vascular disease and infection, the previous studies also found that the risk of lower extremity amputation in diabetes patients is 15 to 46 times of that in non-diabetes patients.

Natural compounds are advantageous for their abundant supplies and diverse skeletons, and they are important bases for drug development. From 1981 till 2019, nearly half of the new FDA-approved drugs were derived from natural products or their derivatives, for example, cocaine-derived narcotics, morphine-derived analgesics, vincristine, doxorubicin and paclitaxel for treating cancers, and fungus-derived penicillin as antibiotics. Therefore, the present invention actively studies to determine which natural compounds have the potential to be developed as novel drugs for promoting chronic wound healing.

SUMMARY OF THE INVENTION

The present invention is a method for promoting chronic wound healing, comprising administering an effective amount of Bletilla formosana (Hayata) Schltr. extract to a subject in need thereof.

In the present invention, the Bletilla formosana (Hayata) Schltr. extract further combines with a pharmaceutically acceptable carrier of the Bletilla formosana (Hayata) Schltr. extract to form a pharmaceutical composition.

In the present invention, the said chronic wound comprises diabetic wound or Diabetic Foot Ulcer (DFU).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 indicates that the Bletilla formosana (Hayata) Schltr. extract "−W+EA" stimulates cell migration of human foreskin fibroblast cell lines Hs68 effectively. FIG. 1A shows the stained image of cell migration; FIG. 1B shows the line chart of cell migration.

DETAILED DESCRIPTION OF THE INVENTION

Figure 2:
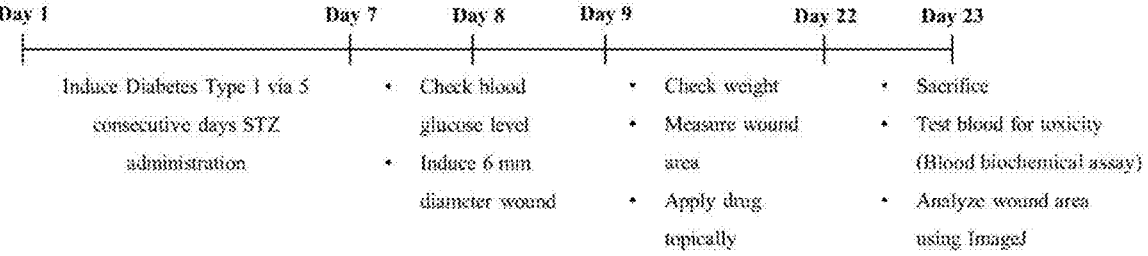
FIG. 2 shows the flow chart of the diabetic wound healing assay.

Bletilla formosana (Hayata) Schltr. is selected as the research target in the present invention.

The present invention is a method for promoting chronic wound healing, comprising administering an effective amount of Bletilla formosana (Hayata) Schltr. extract to a subject in need thereof.

In the present invention, the Bletilla formosana (Hayata) Schltr. extract further combines with a pharmaceutically acceptable carrier of the Bletilla formosana (Hayata) Schltr. extract to form a pharmaceutical composition.

In the present invention, the said chronic wound comprising diabetic wound or Diabetic Foot Ulcer (DFU).

In the present invention, the effective amount of Bletilla formosana (Hayata) Schltr. extract is 0.01 mg/kg-body weight to 100 mg/kg-body weight.

Further, the effective amount of Bletilla formosana (Hayata) Schltr. extract is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 25, 26, 27, 28, 29, 30, 31, 32, 33, 34, 35, 36, 37, 38, 39, 40, 41, 42, 43, 44, 45, 46, 47, 48, 50, 51, 52, 53, 54, 55, 56, 57, 58, 59, 60, 61, 62, 63, 64, 65, 66, 67, 68, 69, 70, 71, 72, 73, 75, 76, 77, 78, 79, 80, 81, 82, 83, 84, 85, 86, 87, 88, 89, 90, 91, 92, 93, 94, 95, 96, 97, 98, or 100 mg/kg-body weight.

In a preferred embodiment, the effective amount of Bletilla formosana (Hayata) Schltr. extract is 1 mg/kg-body weight to 75 mg/kg-body weight.

Preferably, the effective amount of *Bletilla formosana* (*Hayata*) Schltr. extract is 25 mg/kg-body weight to 50 mg/kg-body weight.

In the present invention, the said subject is human or mammal.

When the *Bletilla formosana* (*Hayata*) Schltr. extract is formed to be a pharmaceutical composition, the pharmaceutical composition can comprise pharmaceutically acceptable excipients, especially can further comprise predetermined solvents or oils, PH adjuster and if desired, can further comprise a dispersant. Examples of solvents used in the present invention include, but are not limited to, water, ethanol, isopropanol, 1,3-butanediol, propylene glycol, glycerin, etc. Examples of oils used in the present invention are selected from the group consisting of, but are not limited to, corn oil, sesame oil, flaxseed oil, cottonseed oil, soybean oil, peanut oil, mono-glycerides, di-glycerides, tri-glycerides, mineral oil, squalene, jojoba oil, olive oil, evening primrose oil, borage oil, grape seed oil, coconut oil, sunflower oil, shea butter, and any combinations thereof.

Solvents and oils can be used alone or in any combinations thereof.

Examples of useful dispersants include, but are not limited to, lecithin, organic monoglycerides, sorbitan fatty acid esters, polyoxyethylene fatty acid esters, sorbitan stearate, etc. These raw materials can also be used alone or in any combinations thereof.

In a preferred embodiment of the present invention, the pharmaceutical composition is an injectable preparation or a parenteral and external preparation, wherein the said external preparation comprises but not limited to creams, ointments, gels, washes, patches, inhalant, aerosols, and suppositories etc.

When the pharmaceutical composition is used as an external preparation, an appropriate external skin preparation can be used as a base material, and an aqueous solution, a non-aqueous solvent, a suspension, an emulsion, a gel, a cream, an ointment or a lyophilized preparation, etc., can be used and sterilized according to known methods. The compositions in the form of gels, creams and ointments can be appropriately prepared according to the form of the composition by using known methods, and by addition of known softeners, emulsifiers and thickeners or other materials known in the art.

The gel-form composition can be prepared, for example, by addition of a softener such as trimethylolpropane, polyethylene glycol and glycerol, for example, a solvent of propylene glycol, ethanol and isocetyl alcohol, and pure water.

As used herein, the term "Effective amount" is the amount that can achieve effective results when administered to an individual, or that has the desired activity in vivo or in vitro. In the case of promoting chronic wound healing, as compared to no treatment or vehicle group, effective clinical outcomes include amelioration of the extent or severity of the symptoms associated with the disease or condition, and/or prolonging the life of an individual and/or improvement of the quality of life of the individual.

Description of Embodiments

The present embodiment only records the best example but not intended to limit the present invention.

Preparation of *Bletilla Formosana* (*Hayata*) Schltr. Extract

In the present invention, the *Bletilla formosana* (*Hayata*) Schltr. sample used in the preparation of extract was selected from the roots, the stems, or the leaves of *Bletilla formosana* (*Hayata*) Schltr., or the mixture of its roots, stems, and leaves. The said *Bletilla formosana* (*Hayata*) Schltr. sample was stored at −20° C. after dried and ground until it was ready for use.

In the present invention, firstly, *Bletilla formosana* (*Hayata*) Schltr. sample was added into double-distilled water (ddH$_2$O) at room temperature and then performed ultrasound shock, an upper layer supernatant and a residue were obtained. The residue was purified and extracted by ethyl acetate after frozen and dried, then obtained the *Bletilla formosana* (*Hayata*) Schltr. extract of the present invention and named "−W+EA".

In Vitro Wound Healing Assay

In the present invention, −W+EA was used for evaluating the in vitro wound healing ability.

Human foreskin fibroblast cell lines Hs68 (purchased from Bioresource Collection and Research Center; BCRC No.: 60038) were cultured in Dulbecco's Modified Eagle's Medium (DMEM) with 10% fetal bovine serum (FBS) and 1% Penicillin/Streptomycin (P/S), cells were culture in incubator with the condition of 37° C., 5% CO$_2$.

The Hs68 cells were cultured in 24-wells culture plate, cells were separated to 3 groups, named control group (Basal), low-dosage −W+EA group (0.1 μg/mL−W+EA administered) and high-dosage −W+EA group (1 μg/mL−W+EA administered), respectively. IBIDI Culture-Inserts (purchased from GmbH, Germany) were then used for in vitro wound healing assay according to the manufacturer's instructions.

IBIDI Culture-Inserts were put into well of 24-wells culture plate and gently pressed at the top to ensure close attachment of the IBIDI Culture-Inserts and the well. IBIDI Culture-Inserts are composed of two wells separated by a 500 μm thick wall. Equal amounts of Hs68 cells (4.5×10$^4$ cells) were separated the two wells of IBIDI Culture-Inserts and were cultured for 24 hours, replaced the culture medium to FBS-free medium, gently removed the IBIDI Culture-Inserts to form a 500 μm gap, and washed by Phosphate-buffered saline (PBS).

The nucleus was stained by 2 μg/mL Hoechst 33342 for 10 minutes, and then washed by 1×PBS. The nucleus-stained cells were treated with 0.1 μg/mL−W+EA and 1 μg/mL−W+EA, respectively, and the cell migration was observed by Citation 5 image system (Biotek, England) at 0, 6, 9, 12 and 24 post-treatment.

As shown in FIG. 1A and FIG. 1B, compared to control group, the cell migration was observed in both low-dosage −W+EA group and high-dosage −W+EA group, which demonstrated that −W+EA effectively promotes wound healing.

Diabetic Wound Healing Assay

All the animal experiments of the present invention were performed under the approval of IACUC, Chang Gung University.

The flow chart of the diabetic wound healing assay of the present invention is shown in FIG. 2.

In the beginning, 8-9-week-old C57BL/6 male mice with weight of 20-25 grains were selected for establishing the diabetic animal models of the present invention. After 4 hours fast, the mice were injected intraperitoneally with 55 mg/kg weight of Streptozotocin (STZ) dissolved in pH4.5 citrate buffer for 5 consecutive days. During the STZ injection, normal food and 3% glucose water were given in the first 4 days to induce diabetes, and general water was given instead of glucose water on the last day.

In the above schedule, 72 hours after STZ injection, the mice were fasted for 4 hours, pierced the tail to bled and measured fasting plasma glucose value with the Contour Plus portable blood glucose meter (Ascensia, United Kingdom). Mice with fasting plasma glucose value of 150-250 mg/dL were considered prediabetes, and mice with fasting plasma glucose value >250 mg/dL were considered diabetes and used for the subsequent experiments. The fasting plasma glucose value of all mice were >250 mg/dL.

After the diabetic animal models were established, the diabetic wound healing animal models were established.

A total of 20 male C57BL/6 diabetic mice were used in the experiments, and they were randomly divided into 4 groups, named: untreated group (5 mice), vehicle group (25% Pluronic F-127 and DMSO mixture, 5 mice), low-dosage −W+EA group (25 mg/kg−W+EA, 5 mice) and high-dosage −W+EA group (50 mg/kg−W+EA, 5 mice).

The hair of diabetic mice in dorsal region was removed under anesthesia by razor and using a depilatory cream, medical tape was applied to the dorsal skin to prevent skin stretching. A sterile biopsy punch was then used to create two full-thickness wounds, one on the left and one on the right, each with a diameter of 6 mm.

During the experimental process, all wounds were secured with medical tape that had a circular notch to maintain the wound's gap. The medical tape was used to secure the skin around the wound, preventing skin shrinkage during wound healing, which could affect the calculation of the wound area. The wound on the left side did not receive any treatment, while the wound on the right side was treated daily with the vehicle group solution (25% Pluronic F-127 and DMSO mixture), 25 mg/kg of −W+EA, and 50 mg/kg of −W+EA for two weeks, with daily photographs of the wounds.

The wound area was measured by using Image J analysis software according to the pictures photographed daily and was expressed as the percentage of wound healing compared to day 0.

Figure 3A:
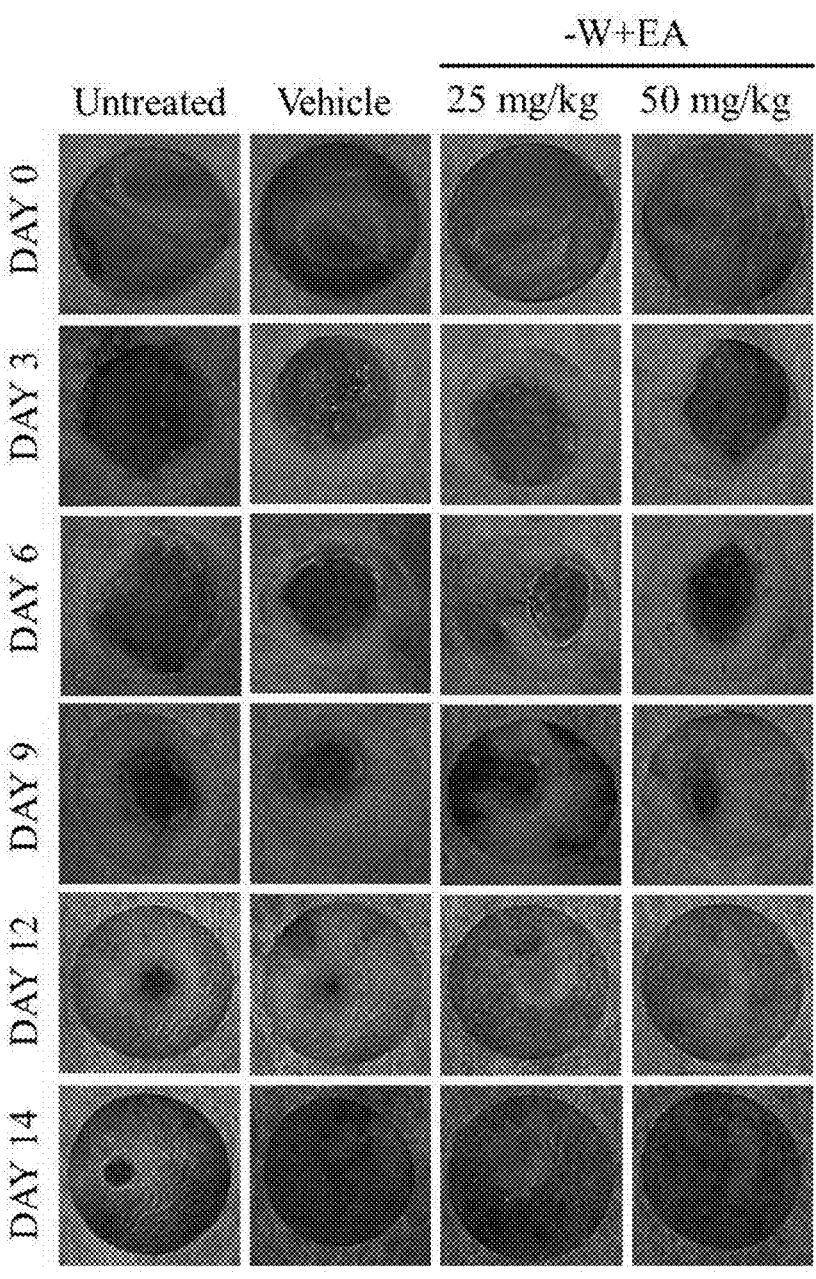
FIG. 3A shows the images of wound healing of untreated group, control group and −W+EA treated groups.
Figures 3, 3B:
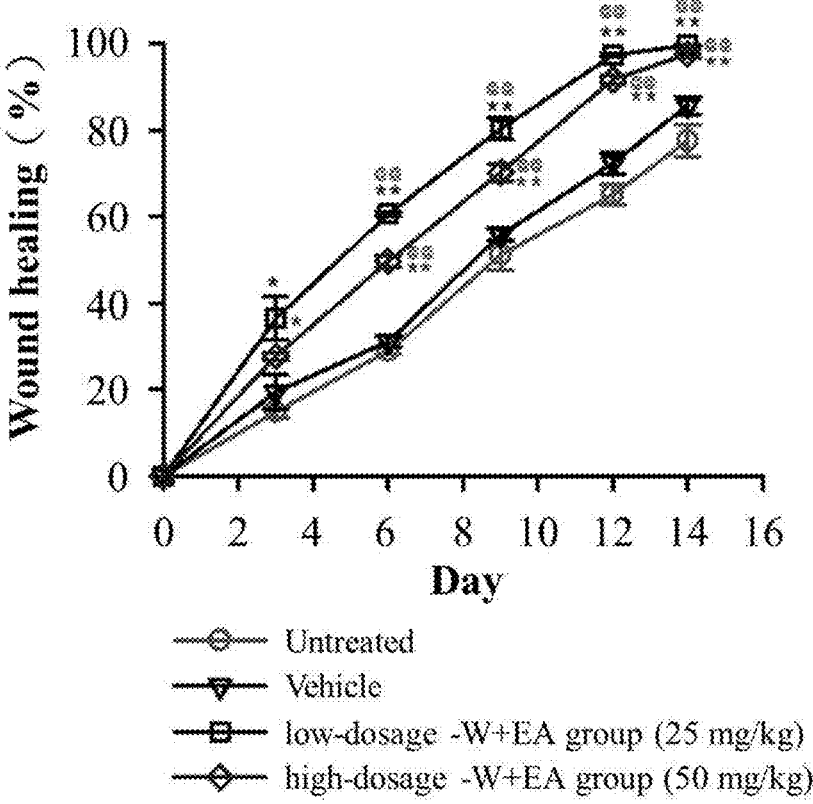
FIG. 3 shows the effect of healing for diabetic wound of the Bletilla formosana (Hayata) Schltr. extract "−W+EA".
FIG. 3B shows the line chart of wound healing rate of untreated group, control group and −W+EA treated groups. *: $p<0.05$ and **: $p<0.01$ indicate significant difference when compared to untreated group. Whereas @: $p<0.05$ and @@: $p<0.01$ indicate significant difference when compared to vehicle group.

The results of wound healing are shown in FIG. 3A and FIG. 3B. FIG. 3A shows the wound healing photographs of the untreated group, vehicle group, low-dosage −W+EA group and high-dosage −W+EA group, and FIG. 3B presents the quantified wound areas illustrated in a line chart. It was observed that, compared to the untreated and vehicle groups, the mice treated with −W+EA exhibited significant wound healing efficacy.

Figure 4:
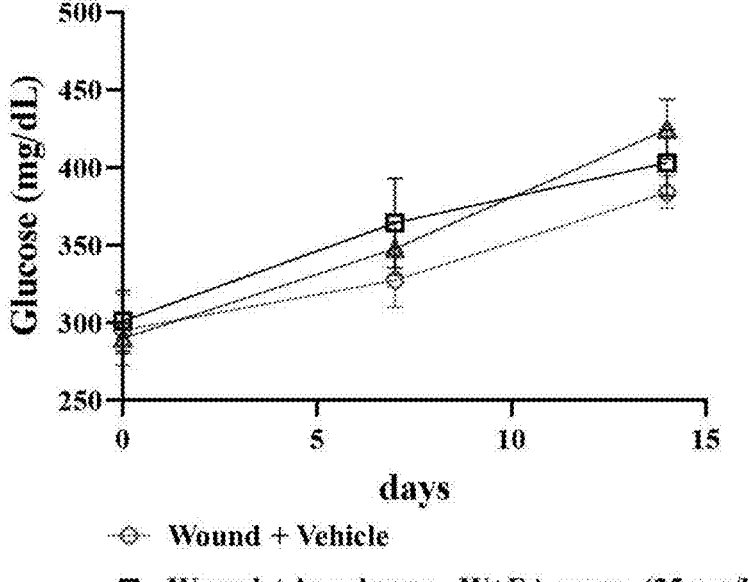
FIG. 4 indicates that the topical application of −W+EA solely promotes the healing of diabetic wounds and does not treat diabetes itself.

To further ascertain that the topical application of −W+EA solely promotes the healing of diabetic wounds and does not treat diabetes itself, fasting blood glucose levels of each mouse were measured during the first and second weeks. Results showed in FIG. 4, the fasting blood glucose levels of all mice continued to rise, confirming that, under the conditions of topical application of −W+EA, it only facilitated the healing of diabetic wounds and did not treat diabetes.

Blood Biochemical Assay

Figure 5:
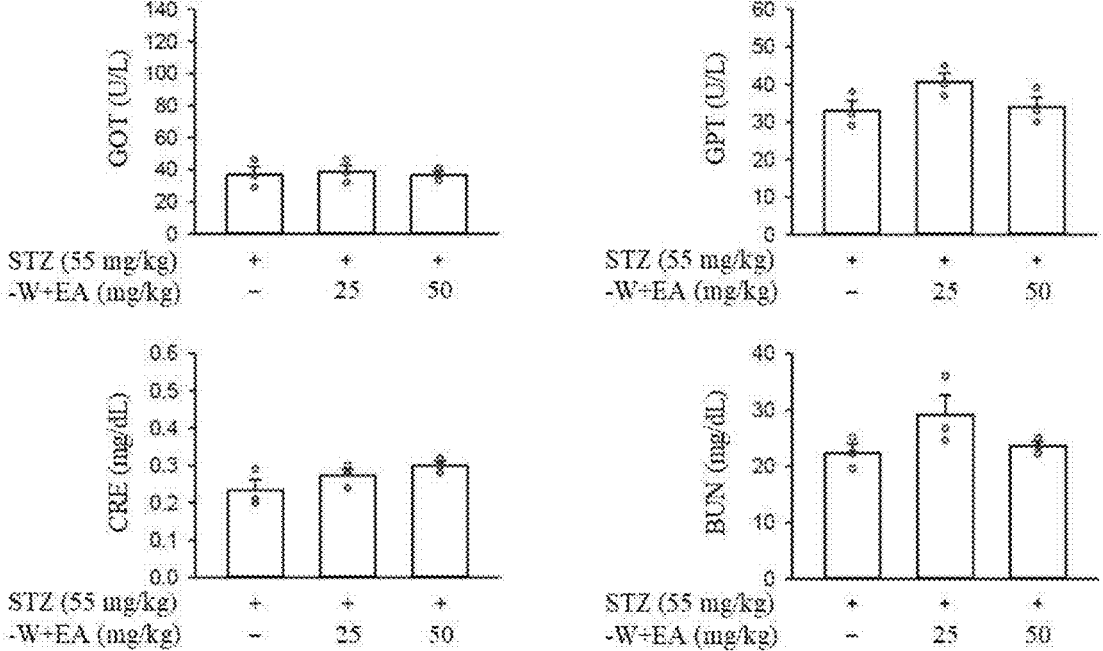
FIG. 5 shows the blood biochemical assay of −W+EA for the experimental animals.

As shown in FIG. 5, through the blood biochemical values, it can be observed that −W+EA did not cause hepatotoxicity (indicated by GOT and GPT levels) or nephrotoxicity (indicated by CRE and BUN levels) in the experimental animals. This indicates that the −W+EA of the present invention has a high safety profile for experimental animals.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cells, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method for promoting chronic wound healing, comprising administering an effective amount of *Bletilla formosana* (*Hayata*) Schltr. extract to a subject in need thereof, wherein the *Bletilla formosana* (*Hayata*) Schltr. is extracted by water, and the residue is re-extracted by ethyl acetate to obtain the *Bletilla formosana* (*Hayata*) Schltr. extract.

2. The method of claim 1, wherein the *Bletilla formosana* (*Hayata*) Schltr. extract further combines with its pharmaceutically acceptable carriers to be a pharmaceutical composition.

3. The method of claim 2, wherein the pharmaceutical composition is a parenteral or external preparation.

4. The method of claim 2, wherein the pharmaceutical composition is a skin topical preparation.

5. The method of claim 1, wherein the effective amount is 0.01 mg/kg weight to 100 mg/kg weight.

6. The method of claim 1, wherein the effective amount is 1 mg/kg weight to 75 mg/kg weight.

7. The method of claim 1, wherein the effective amount is 25 mg/kg weight to 50 mg/kg weight.

8. The method of claim 1, wherein the chronic wound comprises diabetic wound.

9. The method of claim 1, wherein the chronic wound comprises Diabetic Foot Ulcer.

* * * * *